United States Patent [19]
Suda et al.

[11] Patent Number: 5,727,549
[45] Date of Patent: Mar. 17, 1998

[54] MULTI PURPOSE SENSOR

[75] Inventors: Shin Suda; Toru Kurata, both of Tokyo, Japan

[73] Assignee: Nihon Kohden Corporation, Tokyo, Japan

[21] Appl. No.: 531,073

[22] Filed: Sep. 20, 1995

[30] Foreign Application Priority Data

Sep. 22, 1994 [JP] Japan .................................. 6-227676

[51] Int. Cl.[6] ........................................................ A61B 5/05
[52] U.S. Cl. ........................ 128/640; 128/671; 128/701; 128/687
[58] Field of Search .................... 128/639–641, 128/670, 671, 672, 687, 716, 721, 722, 675; 338/2–4

[56] References Cited

U.S. PATENT DOCUMENTS

| 4,570,637 | 2/1986 | Gomes et al. | 128/639 |
|---|---|---|---|
| 4,660,562 | 4/1987 | Hause, Sr. | 128/670 |
| 4,932,265 | 6/1990 | Skuratovsky et al. | 338/4 |
| 4,974,596 | 12/1990 | Frank | 128/672 |
| 5,184,515 | 2/1993 | Terry et al. | 338/4 |
| 5,330,527 | 7/1994 | Montecalvo et al. | 128/639 |
| 5,349,867 | 9/1994 | Park | 338/4 |
| 5,406,952 | 4/1995 | Barnes et al. | 128/690 |
| 5,467,768 | 11/1995 | Suda et al. | 128/640 |

*Primary Examiner*—Robert L. Nasser
*Attorney, Agent, or Firm*—Sughrue, Mion, Zinn, Macpeak & Seas, PLLC

[57] ABSTRACT

A multi-purpose sensor includes a conductive material processed in a fibrous form, a fixing member for fixing the conductive material on a surface of a living body, a pair of electrodes for detecting a movement in the living body as the change in the electric resistance of the conductive material, said one pair of electrodes are attached to one surface of said conductive material.

7 Claims, 10 Drawing Sheets

MULTI PURPOSE SENSOR

BACKGROUND OF THE INVENTION

1. Field of Invention

The present invention relates to a multi-purpose sensor for detecting movements in a living body, as well as bioelectrical phenomena. More particularly, the invention relates to a multi-purpose sensor of a simple construction that is improved in detection precision and which yet consumes less power.

2. Related Art

Conductive rubbers experience changes in electric resistance upon application of pressure and, hence, have been used in pressure-sensitive devices as described in Unexamined Published Japanese Patent Application No. 22829/1992.

However, conductive rubbers have suffered from the defect that they are too hard to be used in sensors of a type that are placed on a living body for detecting weak movements that accompany biological phenomena such as pressure pulse waves and respiration.

On the other hand, fibrous conductive materials, in particular, a carbon fiber felt (CFF) which is prepared by processing carbon fiber in a cotton-like mass is soft enough to be suitable for use as pressure-sensitive devices to detect weak movements in the living body. In addition, CFF has satisfactory electrochemical characteristics and is also available as a biological electrode element. It is known to use CFF as both a pressure-sensitive device and a biological electrode element to construct a multi-purpose sensor by which movements in a living body such as pressure pulse waves and respiration can be measured simultaneously with bioelectrical phenomena such as an electrocardiogram (ECG).

Figure 18:
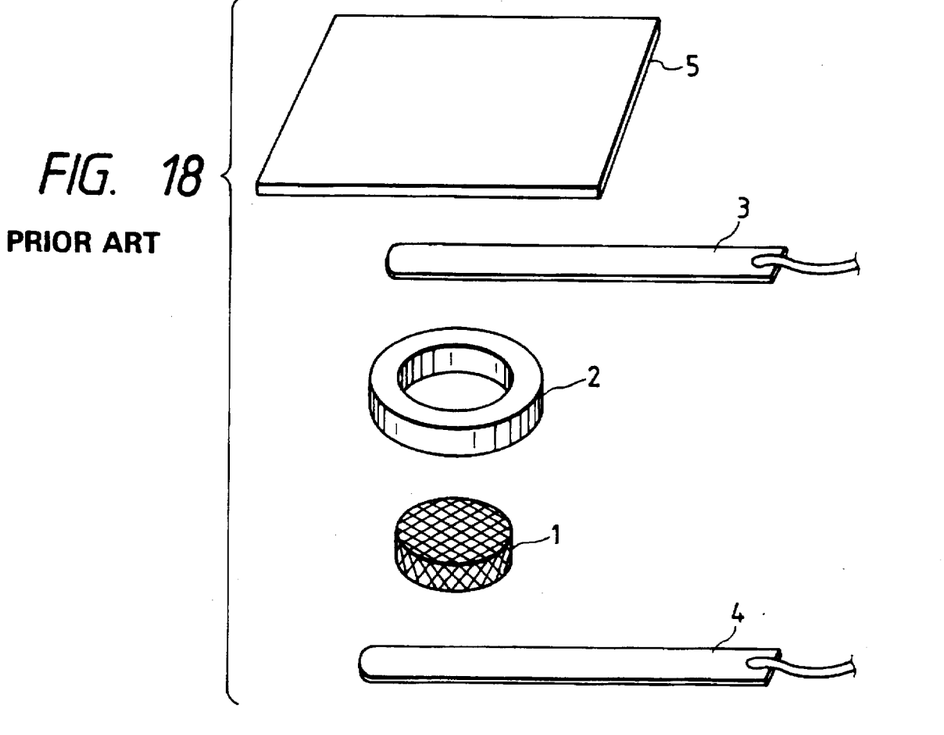
FIG. 18 is a perspective view showing unassembled the construction of a prior art multi-purpose sensor.
Figure 19:
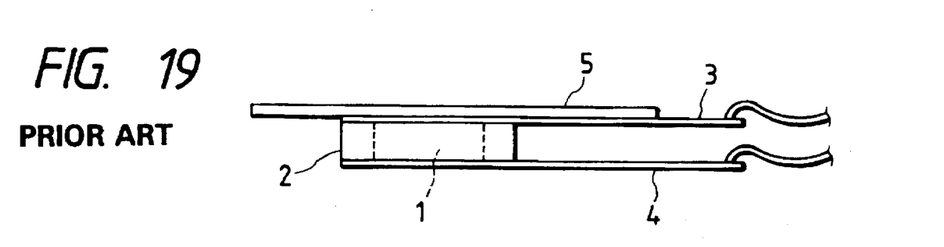
FIG. 19 is a side view of the same multi-purpose sensor in an assembled state.

A conventional type of this multi-purpose sensor is shown schematically in FIGS. 18 and 19. As shown, a cylindrical member of CFF 1 is contained within a ring 2 which is a retaining member formed of an insulator in a cylindrical shape. The opposing end faces of the CFF 1, which is contained the ring 2, are electrically connected to a first electrode terminal 3, serving as a first electrode and made of a conductive material, and a second electrode terminal 4, respectively. The second electrode terminal 4 is made of an insulating material in the form of a film which deforms in accordance with the movement of the patients skin, and serves as a second electrode which is provided with a terminal 4 on a side where the conductive portion is brought into contact with CFF 1. Each terminal has a conducting portion formed on the surface of a film insulator which is to come in contact with the CFF 1. Thus, CFF 1 is held between the terminals 3 and 4. The first terminal 3 has a fixing tape 5 attached thereto. The side of CFF 1 covered with the second terminal 4 is brought into contact with a surface of a living body and both electrodes are secured to the body surface by means of the fixing tape 5. The terminals 3 and 4 are in turn connected to a simple bridge circuit (not shown) to measure the change in electric resistance between the terminals 3 and 4.

With the electrodes thus arranged, a movement in a living body will produce a strain in CFF 1 which, in turn, changes the electric resistance between terminals 3 and 4 by a sufficient amount for detecting a pressure pulse wave or respiration. If other electrodes (not shown) are also attached to the body surface, a bioelectrical phenomenon such as ECG can be measured with the aid of CFF 1 and terminal 3 or 4.

The electrode device of the sandwich type described above has had several problems. Since the surface of CFF 1 which comes in contact with the body surface is partly covered with the second terminal 4, the overall surface area of the biological electrode is reduced to increase the impedance of contact between the body surface and the electrode and the resulting waveform distortion and hum generation will deteriorate the performance of the electrode. If the strain produced in the CFF 1 is comparatively great as in the case of respiratory movements, satisfactory detection is possible with the electrode device of the sandwich type. However, if the phenomenon to be detected is weak as exemplified by peripheral pressure pulse waves, the second terminal 4 interposed between the body surface and the CFF 1 lowers the sensitivity of measurement on account of its stiffness.

To measure pressure pulse waves, a certain pressure must be applied to the electrode but then an inconvenience such as the constriction of a blood vessel or the collapse of the CFF may potentially occur and, in a special case such as hypotension, the sensitivity of measurement may drop to render further detection impossible. Another problem with the electrode system in which CFF 1 is sandwiched between a pair of terminals 3 and 4 is that the second terminal 4 which comes in contact with the body surface and the associated wiring must be prepared in such a way they will cause no inconveniences such as dermatopathy, but then this adds to the complexity of the overall construction of the device. In addition, the conventional electrode device requires a minimum of five components and the number of fabrication steps and, hence, the production cost will increase accordingly. What is more, the second terminal 4 and the associated wiring will prevent CFF 1 from deforming in response to a slight movement in the living body, whereby the sensitivity of detecting movements in the living body is lowered. As a final problem, the complex structure is prone to cause frequent troubles in the device.

SUMMARY OF THE INVENTION

The present invention has been accomplished under these circumstances and has as an object providing a low-cost multi-purpose sensor of a simple structure which is capable of detecting movements in a living body with improved sensitivity while achieving consistent detection of bioelectrical phenomena.

The stated object of the invention can generally be attained by the multi-purpose sensor comprising a conductive material processed in a fibrous form and placed on a surface of a living body by means of a fixing member and which detects a movement in said living body as the change in the electric resistance of said conductive material via a pair of electrodes, wherein said one pair of electrodes are attached to one surface of said conductive material.

This multi-purpose sensor may be modified such that said conductive material is a carbon fiber felt prepared by processing carbon to a cotton-like mass.

The multi-purpose sensor may be modified such that said conductive material is retained on the periphery by means of a holding member.

The multi-purpose sensor may be modified such that an element formed of a second conductive material in a sheet is attached to the face of the first mentioned conductive material which is to come in contact with said living body.

The multi-purpose sensor of the present invention may be modified such that, wherein an electrolyte layer in a gel form is provided on the face of said element which is to come in contact with said living body.

The multi-purpose sensor of the present invention may be modified such that said electrolyte layer in a gel form is surrounded with a ring on the periphery.

Operation:

With the multi-purpose sensors of the present invention, most of the current used for measuring the resistance of CFF is distributed in the sheet region that faces the pair of terminals; this contributes to a higher dc resistance of CFF and one may allow a smaller current for measurement to flow through the bridge circuit. Since respiration and ECG need to be measured not only at rest but also during walking, a battery-driven instrument such as a telemeter is used for measurement and the need to flow a smaller current for measurement will contribute to an extended battery life.

Given the same amount of change in the thickness of CFF, the multi-purpose sensors of the present invention will produce a greater change in dc resistance than the prior art device and this contributes to a better sensitivity of measurement. As a further advantage, the surface of CFF which is to come in contact with the body surface is not covered by either terminal and, hence, the impedance of contact between CFF and the body surface can be sufficiently reduced to improve not only the capability of ECG measurement but also the precision of measurement of weak movements in a living body.

With the multi-purpose sensor of the present invention, the holding member retains the posture of the CFF such that there will occur only small changes in the sensitivity of the measurement even if the device is attached to the subject for a prolonged time.

With the multi-purpose sensor of the present invention, element formed of a second conductive material in a sheet is attached to the face of CFF which is to come in contact with a surface of a living body and this not only contributes to an enhanced capability for recording bioelectrical phenomena but also prevents the permeation of sweat through the CFF which would otherwise deteriorate the performance of the electrode device.

With the multi-purpose sensor of the present invention, the electrolyte layer in a gel form is provided on the face of the element 11 which is to come in contact with the living body and this contributes to a further improvement in the capability of the electrode for measuring bioelectrical phenomena.

With the multi-purpose sensor of the present invention, the periphery of the electrolyte layer is surrounded with ring 31 and this insures that a liquid electrolyte having an even lower impedance of contact with the body surface can be put to service for an extended period of time, thereby achieving a further improvement in the capability of the electrode for measuring bioelectrical phenomena.

DETAILED DESCRIPTION OF THE PREFERRED EMBODIMENTS

The preferred examples of the multi-purpose sensor according to the invention will now be described with reference to FIGS. 1 to 17, in which the parts or components which are the same as or equivalent to those shown in FIGS. 18 and 19 (the prior art) are identified by like numerals and will not be described in detail.

Figure 1:
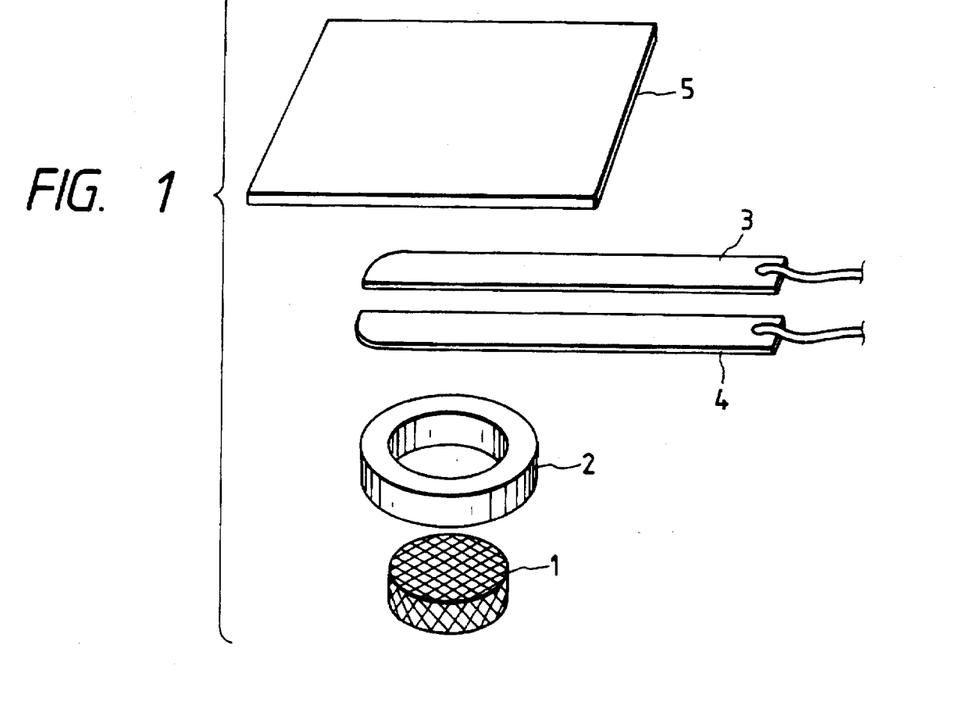
FIG. 1 is a perspective view showing unassembled the multi-purpose sensor according to the first example of the invention.
Figure 2:
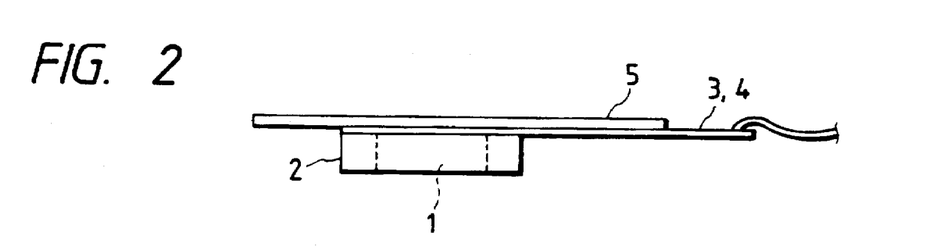
FIG. 2 is a side view of the same multi-purpose sensor in an assembled state.
Figure 3:
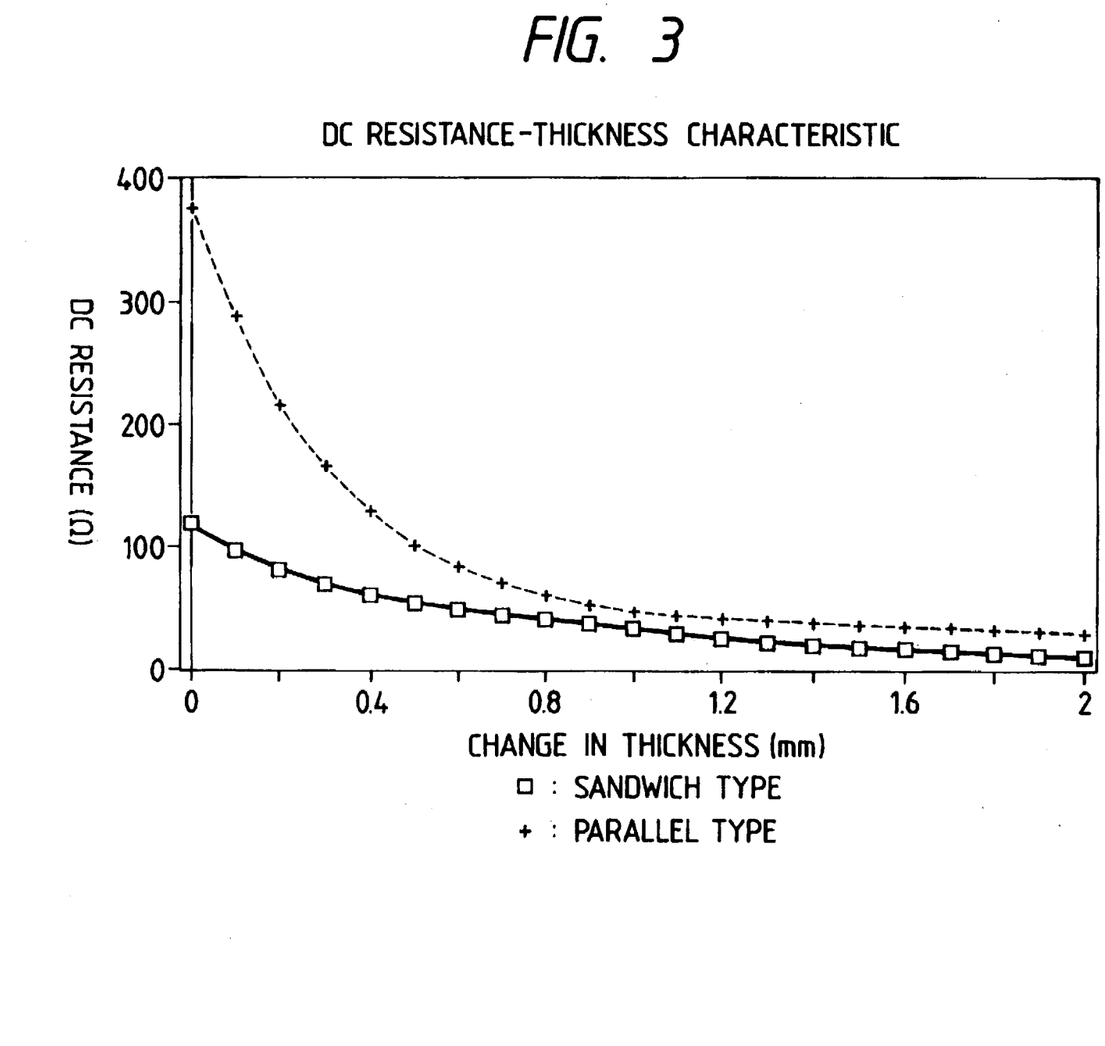
FIG. 3 is a graph showing the dc resistance of CFF electrodes in the multi-purpose sensor of FIGS. 1 and 2 as a function of the electrode thickness.

FIGS. 1 and 2 show the construction of a multi-purpose sensor according to the first example of the invention. As shown, the first example is characterized in that a pair of terminals 3 and 4 which are formed of a conductive material such as a metal in a rectangular plate form are spaced parallel to each other and attached to the side of CFF 1 opposite to the side which is to be placed on a living body.

Figure 4:
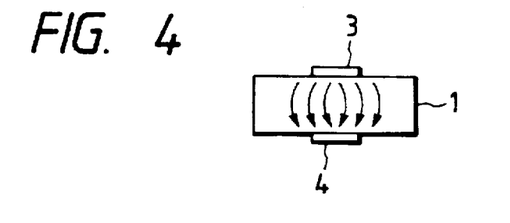
FIG. 4 is a sketch showing the distribution of a current for measurement in an electrode device of the sandwich type.
Figure 5:
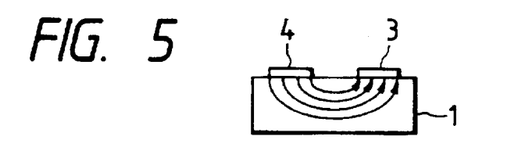
FIG. 5 is a sketch showing the distribution of a current for measurement in an electrode device of the parallel type.

With the conventional electrode device of a sandwich type, the current for measuring the resistance of CFF 1 flows through the entire part of CFF 1 as illustrated in FIG. 4. However, with the parallel electrode device in the first example of the invention, most of the current for measuring the resistance of CFF 1 is distributed in the sheet region facing the pair of terminals 3 and 4 as shown in FIG. 5. As a result, the dc resistance of CFF 1 is greater in the parallel electrode device than in the sandwich type (see the graph in FIG. 3) and, hence, a smaller amount of current for measurement to be flowed into the bridge circuit.

As already noted, respiration and ECG need to be measured not only at rest but also during walking and a battery-driven instrument such as a telemeter is used to meet this need. Hence, the current for measurement is desirably held to a minimum level in order to extend the battery life. In this respect, the parallel electrode device of the invention which requires only a small amount of current for measurement would be suitable for use in a telemeter and other battery-driven ECG respiration monitor equipment.

Figure 6:
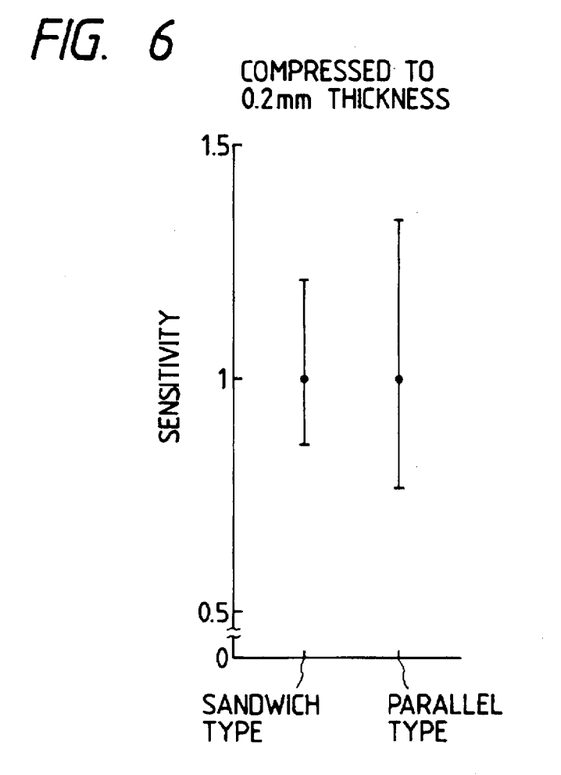
FIG. 6 is a graph comparing the sensitivities of the sandwich and parallel types in the case where the CFF electrodes were compressed to a thickness of 0.2 mm.
Figure 7:
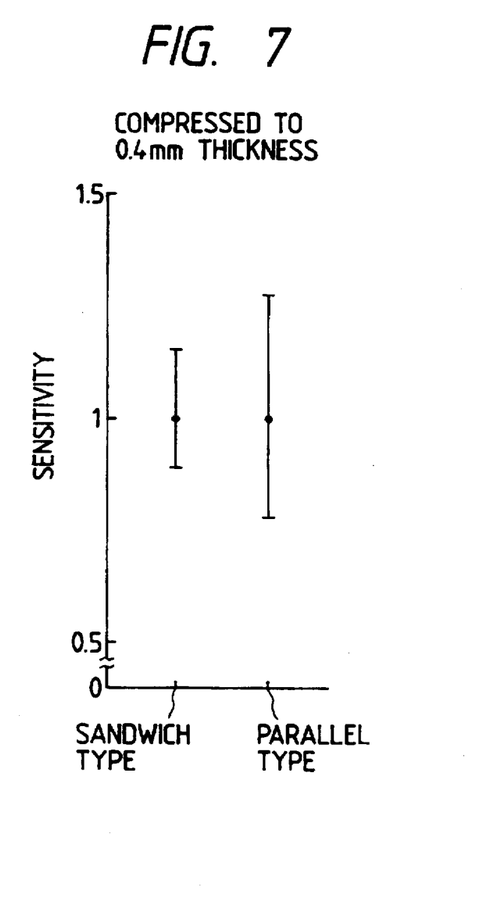
FIG. 7 is a graph comparing the sensitivities of the sandwich and parallel types in the case where the CFF electrodes were compressed to a thickness of 0.4 mm.
Figure 8:
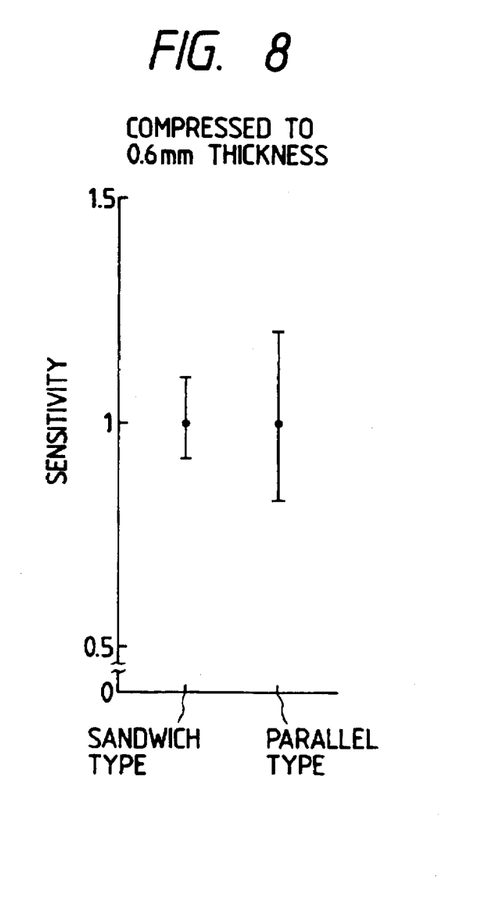
FIG. 8 is a graph comparing the sensitivities of the sandwich and parallel types in the case where the CFF electrodes were compressed to a thickness of 0.6 mm.

Given the same amount of change in the thickness of CFF 1, the parallel electrode device produces a greater change in dc resistance than the sandwich version and, hence, the former has a sensitivity of measurement which is 1.5 to 2 times the value for the latter (see FIGS. 6 to 8). Thus, the parallel electrode device can achieve a comparable sensitivity to the sandwich version with a smaller current flow. FIGS. 6 to 8 are graphs comprising the sensitivities of two types of electrode device with CFF 1. The sensitivity is defined by $(R+\Delta R)/R$ where R is the resistance of CFF 1 being compressed by varying thicknesses of 0.2 mm, 0.4 mm and 0.6 mm and $\Delta R$ is the change in its resistance that occurs when the compressed CFF 1 is released or, further compressed to produce a thickness change of 0.1 mm.

Another advantage of the parallel electrode device is that the surface of CFF 1 which is to come in contact with the body surface is not covered with terminal 4 and, hence, the impedance of contact between body surface and the electrode can be reduced to from one half to a third of the value from the sandwich version. This contributes to a better performance in ECG measurement with the device being used as a lead electrode.

To insure that CFF 1 is brought into contact with the body surface over an area comparable to that achieved by the sandwich version having an electrode diameter of about 20 mm, the parallel version needs only an electrode diameter of about 16 mm; thus, the parallel electrode device is available in a compact size.

The parallel electrode device has the added advantage in that the propagation of pressure changes from the side of CFF 1 in contact with the body surface is not interfered with by interposed elements such as terminals 3 and 4 and, hence, weak movements in the living body such as peripheral pressure pulse waves can be measured with greater accuracy.

Figure 9:
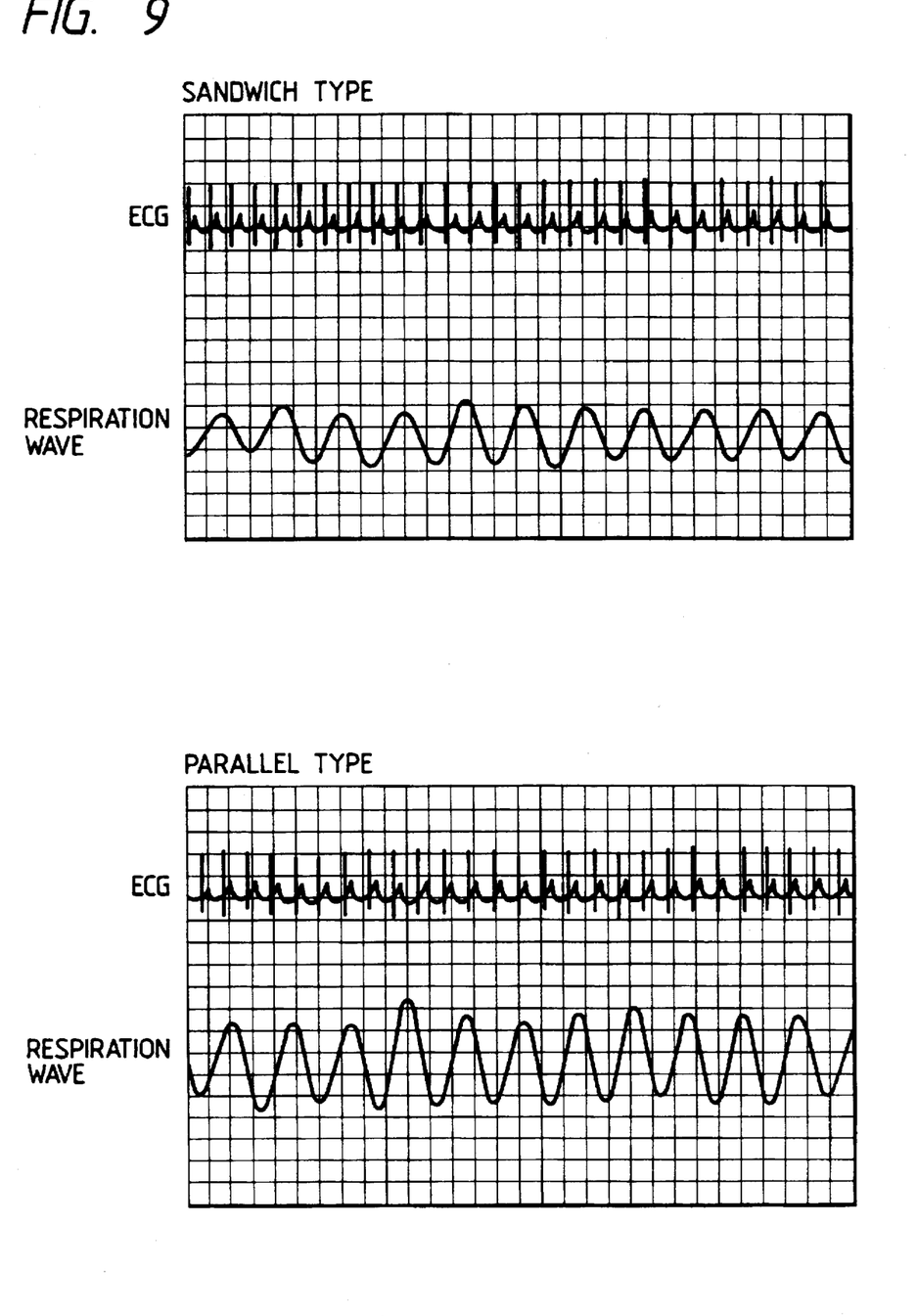
FIG. 9 shows graphically exemplary data for the measurement of ECG and respiration curves using electrode devices of the sandwich and parallel types.

FIG. 9 shows exemplary data as obtained by simultaneous recording of the respiratory movement and ECG with two types of electrode devices, the sandwich type and the parallel type. Obviously, the parallel type had a higher sensitivity for the respiratory movement than the sandwich type.

Figure 10:
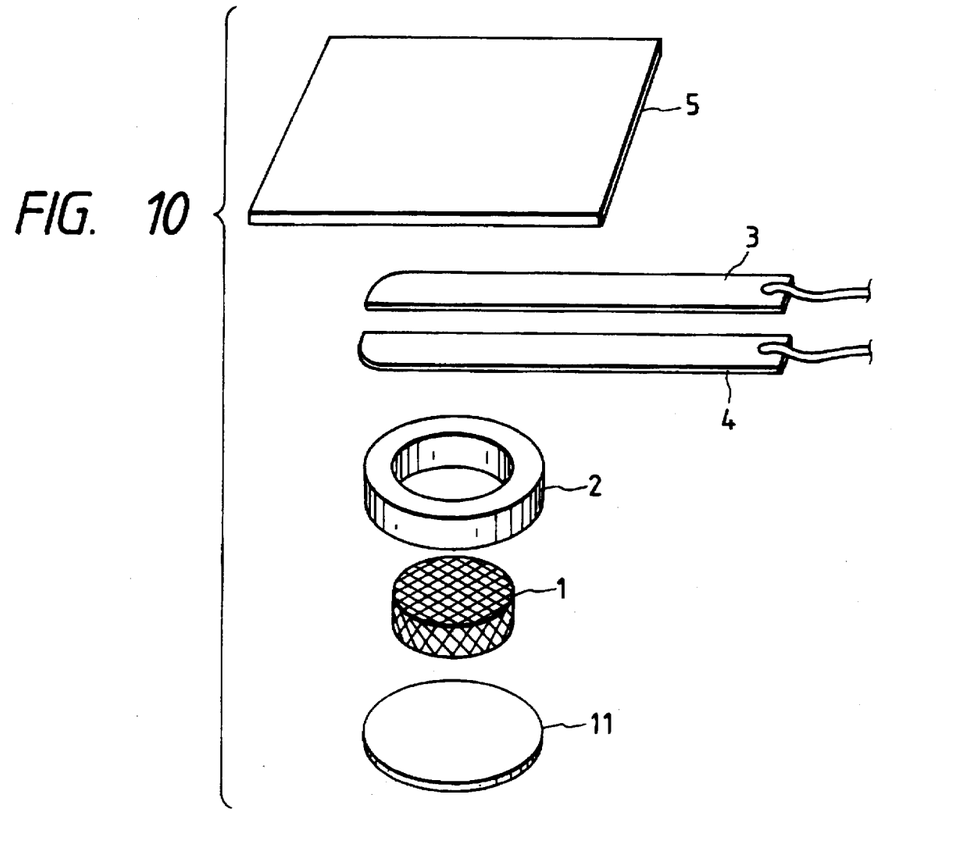
FIG. 10 is a perspective view showing unassembled the multi-purpose sensor according to the second example of the invention.
Figure 11:
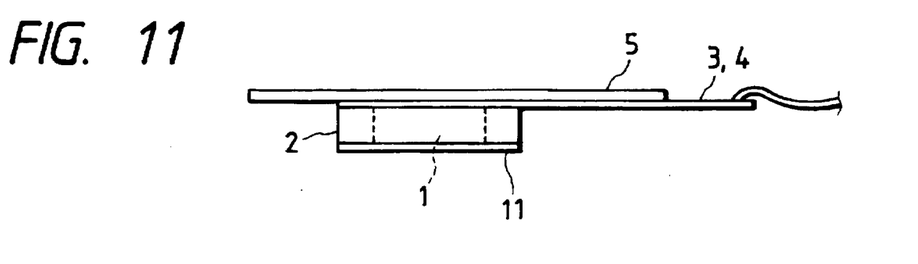
FIG. 11 is a side view of the same multi-purpose sensor in an assembled state.

FIGS. 10 and 11 show the construction of a multi-purpose sensor according to the second example of the invention. As shown, the second example is characterized in that an element 11 formed of a conductive material in a sheet is attached to the end faces of CFF 1 and ring 2 that are to come in contact with the body surface. The conductive material may be selected from among foils of metals such as silver, silver/silver chloride, tin and aluminum, conductive films and conductive plastics. The design of the second example is used in the case where the movement in a living body to be measured is large as typified by the respiratory movement and where there is no need to increase the precision of measurement. In this case, the provision of element 11 enhances the capability of the device for recording bioelectrical phenomena such as ECG and EMG (electromyogram); at the same time, the element 11 prevents the permeation of a subject's sweat through the CFF 1 which would otherwise deteriorate the electrode performance in measuring the movements in a living body.

Figure 12:
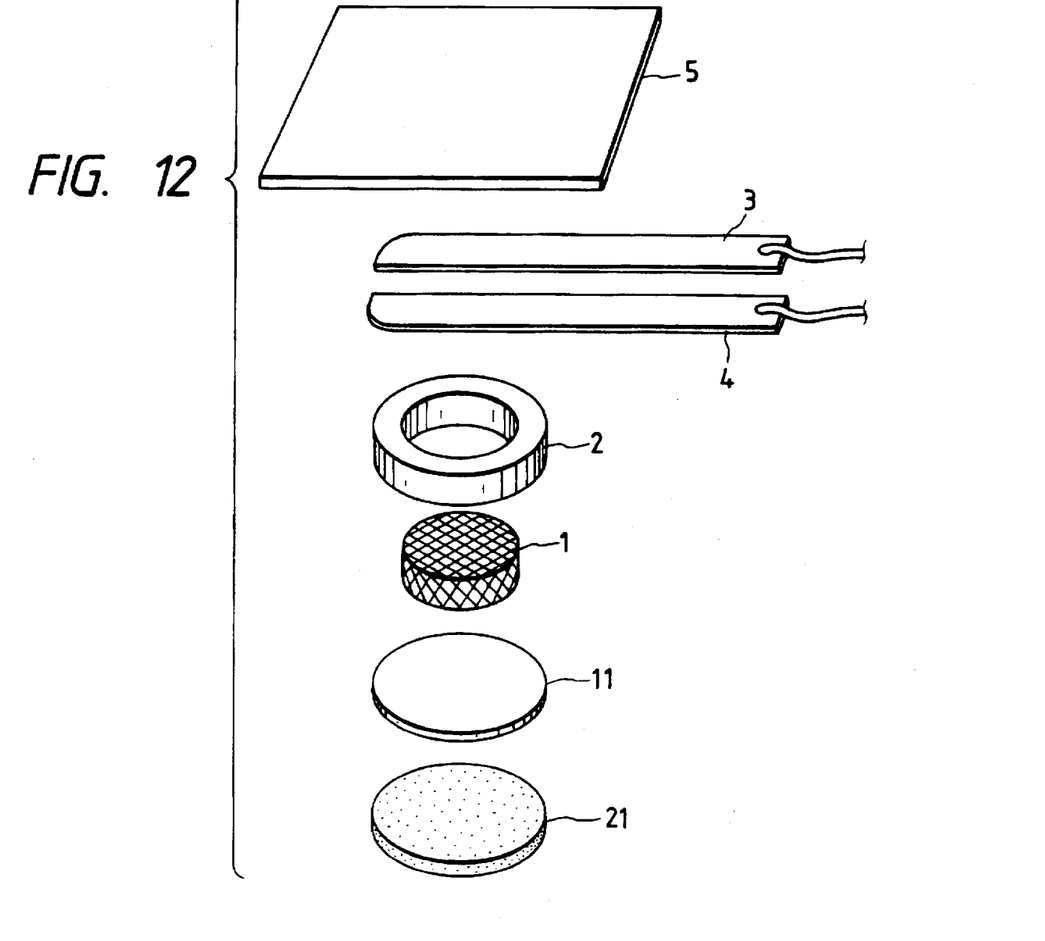
FIG. 12 is a perspective view showing unassembled the multi-purpose sensor according to the third example of the invention.
Figure 13:
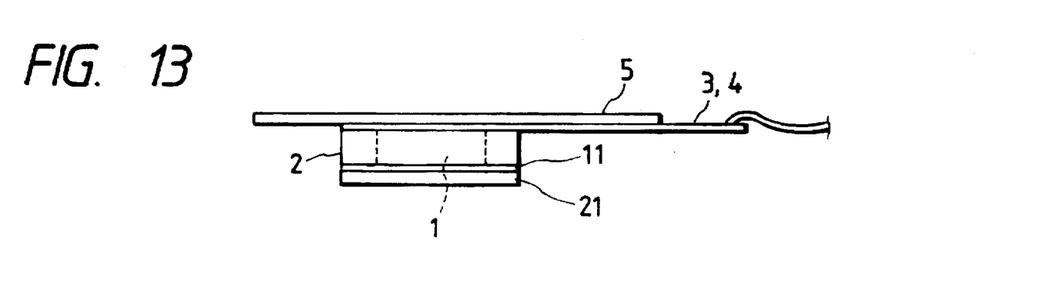
FIG. 13 is a side view of the same multi-purpose sensor in an assembled state.

FIGS. 12 and 13 show the construction of a multi-purpose sensor according to the third example of the invention. As shown, the third example is characterized in that an electrolyte layer 21 such as in a solid gel form is provided on the side of the element 11 (FIGS. 10 and 11) which is to come in contact with the body surface. The design of the third example contributes to a further improvement in the electrode performance in recording bioelectrical phenomena.

Figure 14:
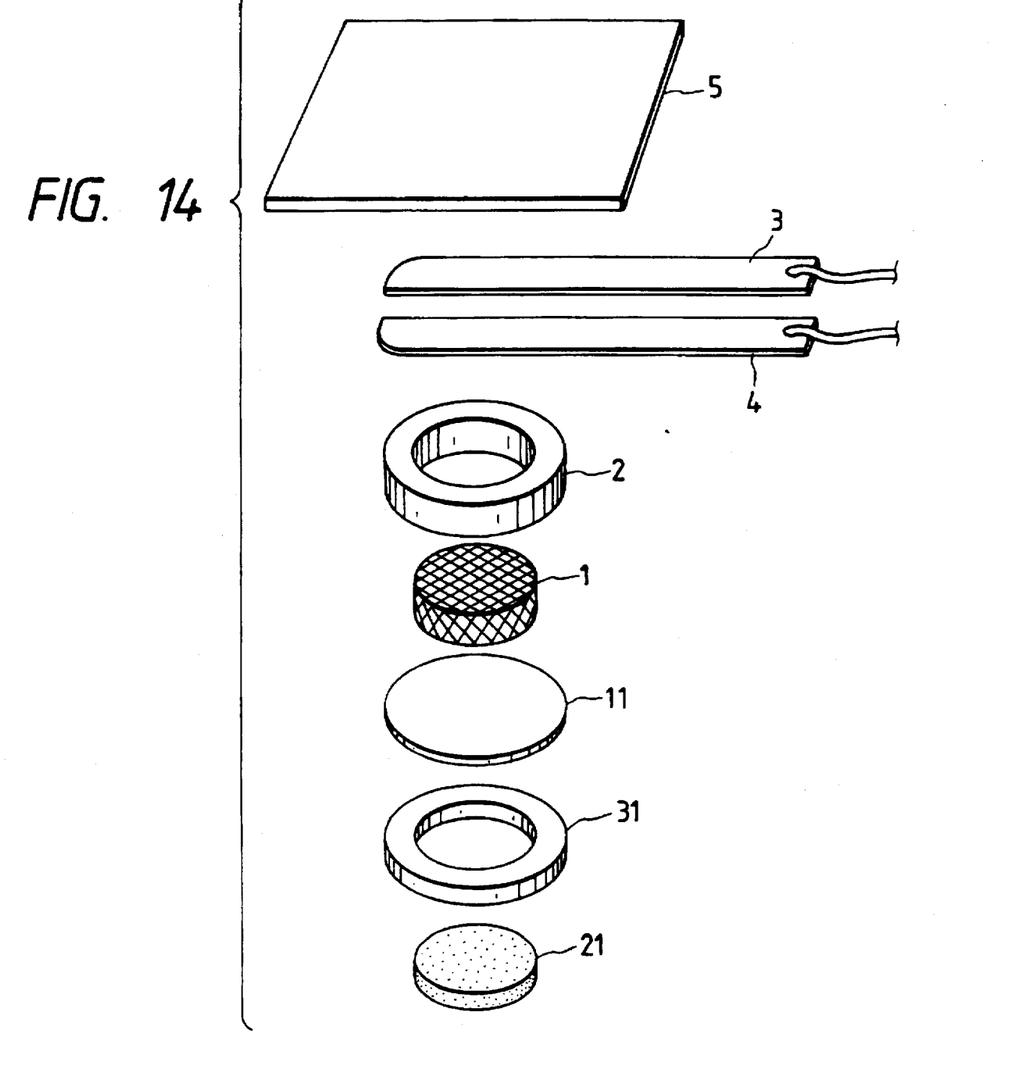
FIG. 14 is a perspective view showing unassembled the multi-purpose sensor according to the fourth example of the invention.
Figure 15:
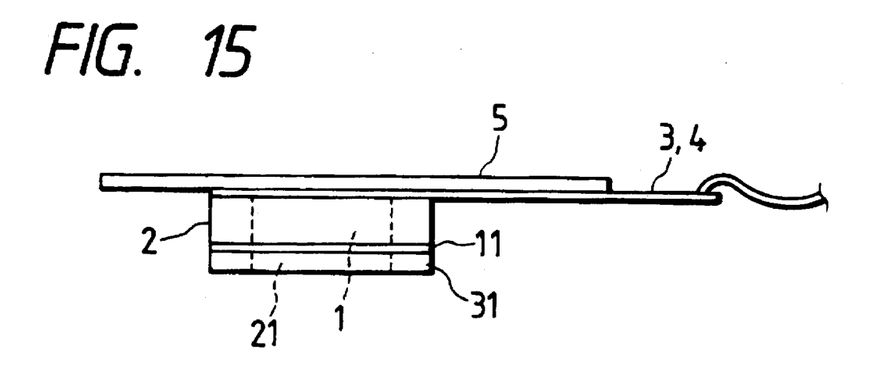
FIG. 15 is a side view of the same multi-purpose sensor in an assembled state.

FIGS. 14 and 15 show the construction of a multi-purpose sensor according to the fourth example of the invention. As shown, the fourth example is characterized by surrounding the periphery of the electrolyte layer 21 (FIGS. 12 and 13) with a ring 31; in addition to the advantage achieved in the third example, the fourth example insures that a liquid electrolyte having an even lower impedance of contact with the living body can be put to service, thus contributing to a further improvement in the electrode performance in recording bioelectrical phenomena.

The foregoing description of the four preferred examples of the invention is directed to the case where CFF 1 is formed as a cylinder of carbon fiber felt which was prepared by processing carbon fiber in a cotton-like mass. It should, however, be noted that CFF 1 need not be in a cylindrical form and may assume a variety of shapes depending on the movement in a living body to be measured and the bioelectrical phenomenon to be measured. Similarly, the shapes of ring 2, element 11 and ring 31 are in no way limited to a circle. The constituent material of CFF 1 also is not limited to carbon and its may be replaced by metals (e.g., stainless steel), conductive polymers (e.g. polyacetylene) or any other conductive materials depending on the parameter or event to be measured. It should also be added that CFF 1 may be formed from combinations of carbon, metals, conductive polymers, etc. The inclusion of non-conductive materials is optional.

Ring 2 may be formed of soft materials that will deform together with CFF 1 if the phenomenon to be measured is the respiratory movement. If there is a need to suppress deformations that will occur around the site of measurement as in the case of detecting localized movements such as peripheral pressure pulse waves, ring 2 may be formed of hard materials. Thus, a suitable material may be chosen in accordance with the specific parameter to be measured.

Figure 16:
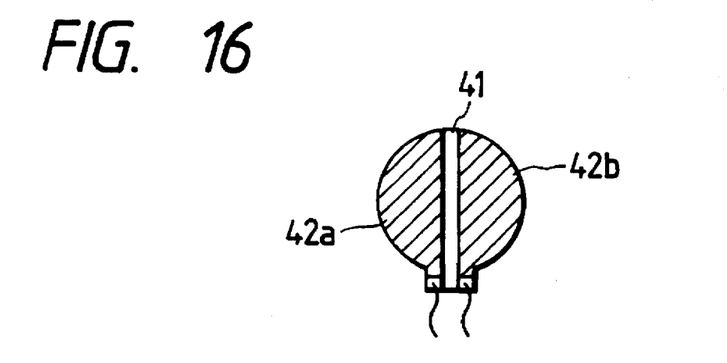
FIG. 16 is a plan view showing a first modification of the terminals in FIG. 1.
Figure 17:
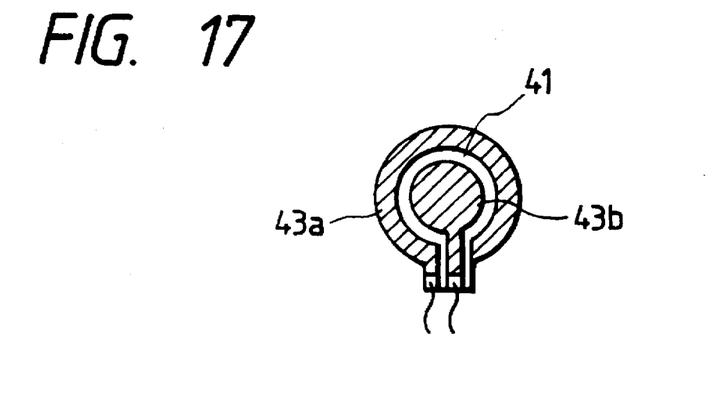
FIG. 17 is a plan view showing a second modification of the terminals in FIG. 1.

The foregoing description of the four preferred examples of the invention also concerns the case where terminals 3 and 4 are formed as two separate rectangular members. It should, however, be noted that those terminals may be replaced by to semi-circular conductive layers 42a and 42b that are provided on an insulating substrate 41 as shown in FIG. 16 or by an annular conductive layer 43a surrounding a central disk of conductive layer 43b as shown in FIG. 17. All that is required is to provide a pair of spaced terminals on the same plane and they may assume a suitable shape in accordance with the specific parameter or event to be measured. In certain applications where particularly high precision of measurement is not required as in the case of measuring the respiratory movement, terminal 4 may be provided on the side of CFF 1 which is to come in contact with a surface of a living body. Thus, the number of parts or components and the production cost can accordingly be reduced. It should further be noted that the shape of the fixing tape 5 is by no means limited to a rectangle and various other shapes may be adopted depending on the parameter or event to be measured and on the site of sensor placement.

The foregoing description assumes the use of a fixing tape as the fixing member but this may be replaced by a fixing band or a device for fixing the limb leads of ECG.

The third example described above is characterized by the provision of electrolyte layer 21 in the second example but said electrolyte layer may be provided in the first example. In this alternative case, there is assured a better electrical contact with the skin than in the first example and, hence, an improvement is achieved in the electrode performance in recording bioelectrical phenomena.

As described on the foregoing pages, the multi-purpose sensor of the invention has a pair of electrodes attached to one surface of a conductive material placed on a surface of a living body and this design improves the precision in the detection of measuring movements in the living body, reduces the power consumption of the instrument, simplifies its construction and reduces the size of electrodes.

What is claimed is:

1. A multi-purpose sensor comprising:

a fibrous conductive material having a first face operative to contact a surface of a living body, said first face being devoid of any electrodes, is adapted to face and a second face which away from the living body;

a pair of electrodes for detecting a movement in the living body as the change in an electric resistance of said fibrous conductive material, said pair of electrodes being attached to said second face of said fibrous conductive material; and a fixing member attached to at least one of said second face of said fibrous conductive material and said pair of electrodes, said fixing member being operative to fix said fibrous conductive material on the surface of the living body.

2. A multi-purpose sensor according to claim 1, wherein said fibrous conductive material comprises a carbon fiber felt prepared by processing carbon fiber into a cotton-like mass.

3. A multi-purpose sensor according to claim 1, further comprising:

a holder member which surrounds and is attached to a periphery of said fibrous conductive material.

4. A multi-purpose sensor according to claim 2, further comprising:

a holder member which surrounds and is attached to a periphery of said fibrous conductive material.

5. A multi-purpose sensor according to any one of claims 1 to 4, further comprising an element formed of a further conductive sheet material attached to the first face of said fibrous conductive material and which in turn is adopted to come in contact with the living body.

6. A multi-purpose sensor according to claim 5, further comprising:

an electrolyte layer in a gel form provided on a surface of said element which is adapted to face the living body.

7. A multi-purpose sensor according to claim 6, further comprising:

a ring which surrounds and is attached to a periphery of said electrolyte layer in a gel form.

* * * * *